(12) United States Patent
Hill

(10) Patent No.: US 7,021,145 B2
(45) Date of Patent: Apr. 4, 2006

(54) ACOUSTIC TRANSDUCER

(75) Inventor: James A. Hill, Haverhill, MA (US)

(73) Assignee: Horiba Instruments, Inc, Irvine, CA (US)

( * ) Notice: Subject to any disclaimer, the term of this patent is extended or adjusted under 35 U.S.C. 154(b) by 168 days.

(21) Appl. No.: 10/623,758

(22) Filed: Jul. 21, 2003

(65) Prior Publication Data

US 2005/0016298 A1    Jan. 27, 2005

(51) Int. Cl.
  *G01N 29/02* (2006.01)
  *G01N 29/28* (2006.01)
  *G01N 1/20* (2006.01)
  *B06B 1/06* (2006.01)
  *G01F 1/66* (2006.01)

(52) U.S. Cl. .................... 73/644; 73/198; 73/632; 73/64.57; 73/863.03; 73/861.18

(58) Field of Classification Search ..................
    73/861.25–861.27, 632, 24.01, 64.53, 861.18,
    73/644, 198, 863.03, 863.81
  See application file for complete search history.

(56) References Cited

U.S. PATENT DOCUMENTS

| | | | | |
|---|---|---|---|---|
| 2,523,691 A * | 9/1950 | Fitch | ............... | 73/863.81 X |
| 3,229,134 A * | 1/1966 | Rakula | ............... | 310/216 |
| 4,287,755 A * | 9/1981 | Mansfield | ............... | 73/644 X |
| 4,297,607 A | 10/1981 | Lynnworth et al. | ......... | 73/142 X |
| 4,336,719 A | 6/1982 | Lynnworth | ............... | 73/861.27 |
| 4,662,215 A | 5/1987 | Eckert | ............... | 73/644 X |
| 4,743,870 A | 5/1988 | Jen et al. | ............... | 333/147 |
| 5,064,299 A * | 11/1991 | Hirschmann et al. | ......... | 385/33 |
| 5,159,838 A | 11/1992 | Lynnworth | ............... | 73/644 |
| 5,217,018 A | 6/1993 | Dias | ............... | 333/154 X |
| 5,241,287 A | 8/1993 | Jen | ............... | 333/143 |
| 5,438,999 A | 8/1995 | Kikuchi et al. | ......... | 310/336 X |
| 5,708,209 A | 1/1998 | Stiffler et al. | ............... | 73/644 |
| 5,756,360 A | 5/1998 | Harvey et al. | ......... | 73/863.03 X |
| 5,951,163 A | 9/1999 | Jen et al. | ............... | 73/547 X |
| 6,296,385 B1 | 10/2001 | Balasubramaniam | ......... | 73/597 X |
| 6,307,302 B1 | 10/2001 | Toda | ............... | 310/334 |
| 6,343,511 B1 | 2/2002 | Lynnworth et al. | ........... | 73/644 |
| 6,343,512 B1 * | 2/2002 | Bourne et al. | ............... | 73/644 |
| 6,643,221 B1 * | 11/2003 | Hsu et al. | ............... | 367/162 |
| 2004/0162546 A1 * | 8/2004 | Liang et al. | ............... | 604/542 |

FOREIGN PATENT DOCUMENTS

| | | | | |
|---|---|---|---|---|
| EP | 352676 A | * | 1/1990 | ........ 374/117 |
| FR | 2735205 A3 | * | 12/1996 | |
| WO | WO 96/41157 | | 12/1996 | |

* cited by examiner

*Primary Examiner*—Thomas P. Noland
(74) *Attorney, Agent, or Firm*—Brooks Kushman P.C.

(57) ABSTRACT

An acoustic transducer for measuring a property of a fluid includes an acoustic pulse generator and buffer assembly. The buffer assembly is between the pulse generator and the fluid. The buffer assembly is composed of a core and a sleeve shrink fitted over the core to form a cladding layer. The cladding layer reduces dispersion of the acoustic pulses traveling through the core.

29 Claims, 4 Drawing Sheets

ACOUSTIC TRANSDUCER

BACKGROUND OF THE INVENTION

1. Field of the Invention

The present invention relates to acoustic transducers, including those used in flow meters.

2. Background Art

Transmitting pulses of acoustic energy through a fluid is useful for measuring the state and properties of the fluid, specifically the velocity and temperature. Piezoceramic elements are commonly used in acoustic transducers to generate ultrasonic acoustic pulses or continuous wave fields. However, these ceramics lose polarization if exposed to temperatures in excess of half of their Curie point. For commercially available ceramics, this limits the operating temperature of the ceramic to under 200° C. To operate in fluids above this temperature, one method is to provide a buffer or delay line between the piezoceramic element and the fluid (for example, exhaust gas) as shown in FIG. 1. FIG. 1 depicts an acoustic transducer 10. Transducer 10 includes piezoceramic element 12 and buffer 14 extending through wall 16 into the fluid which is illustrated as exhaust gas. Thermal energy is dissipated at internal convective boundary layer 18, in buffer 14, and at external convective boundary layer 20 as heat conducts upward in buffer 14 toward piezoceramic element 12. Buffers operate by the principle of Fourier's Law of heat conduction:

$$q''= -\kappa \nabla T,$$

Where q" is the heat flux, κ is the thermal conductivity of the material and T is temperature. Detailed solutions of this equation require numerical methods but with some simplifying assumptions, a buffer system can be reduced to a lumped parameter model that can be represented as the equivalent circuit shown in FIG. 2. FIG. 2 illustrates the exhaust, buffer tip, crystal and ambient temperatures, and the thermal resistances of the external convective boundary layer, buffer, and internal convective boundary layer in a lumped parameter model.

For the lumped parameter model illustrated in FIG. 2, the temperature of the crystal is:

$$T_{crystal} = T_{exhaust} - (T_{exhaust} - T_{ambient}) \frac{(R_{IBL} + R_{buffer})}{R_{IBL} + R_{buffer} + R_{EBL}}.$$

A disadvantage associated with existing buffer systems is that a short buffer has problems when operating with hot fluids, while making the buffer longer requires that the buffer guide the wave front in the desired direction. However, solid buffers fail to effectively guide the acoustic pulse resulting in a dispersive buffer that distorts the ultrasonic pulse and limits the usefulness of the flow meter. A buffer with a solid core and solid cladding created by doping (for example, spray deposition or powder metallurgy) has been proposed. However, the doping techniques used to create the cladding have some disadvantages.

Additional background information may be found in U.S. Pat. Nos. 5,756,360; 4,336,719; 5,217,018; 5,159,838; 6,343,511; 5,241,287; 4,743,870; 5,438,999; 4,297,607; and 6,307,302.

For the foregoing reasons, there is a need for an improved acoustic transducer.

SUMMARY OF THE INVENTION

It is an object of the present invention to provide an acoustic transducer by shrink fitting a coaxial sleeve over a core of low thermal conductivity material.

In carrying out the present invention, an acoustic transducer for measuring a property of a fluid is provided. The acoustic transducer comprises an acoustic pulse generator and a buffer assembly. The buffer assembly is located between the pulse generator and the fluid. The buffer assembly is composed of a core and a sleeve shrink fitted over the core to form a cladding. The cladding reduces dispersion of the acoustic pulses traveling through the core.

The acoustic pulse generator may be a piezoceramic element for generating an ultrasonic pulse. Preferably, the core thermal conductivity is less than 15 W/(m·K). More preferably, the core thermal conductivity is less than 1 W/(m·K). The core may be made of fused silica, and is preferably made of a composite of fused silica and mica. Of course, ceramics or other materials may alternatively be used for the core. By making the core of a light weight, low thermal conductivity material that is more corrosion resistant than the body of the transducer, a metallic sealing layer is not needed and the core may be in direct contact with the fluid which is being measured or have a light anti-reflective surface coating.

The sleeve may be made of metal, and preferably has a thermal conductivity of at least 15 W/(m·K). In a preferred implementation, the sleeve is made of titanium. It is appreciated that the sleeve is shrink fitted over the core to form a cladding. The cladding reduces dispersion of the acoustic pulses traveling through the core. The shrink fitting of the sleeve over the core to form the cladding has advantages over other possible techniques to form a cladding such as spray deposition or powder metallurgy. Using the mechanical technique of shrink fitting provides a suitable cladded core at great cost savings relative to other possible techniques. In accordance with the invention, preferred techniques for securing the sleeve to the core include using a refractory cement and using high temperature glass fusing. The cladding provides the needed gradient in longitudinal sound speed through a medium to reduce dispersion of acoustic pulses traveling through the core.

In a preferred implementation, the acoustic transducer further comprises a thermal management system. The thermal management system is mounted to the sleeve to transfer heat from the sleeve. The thermal management system is formed of a high thermal conductivity material and is arranged along the sleeve such that substantial heat is transferred to the environment from the thermal management system without excessive temperature increase at the pulse generator. The preferred thermal management system includes a plurality of fins mounted to the holder to dissipate heat from the sleeve. The thermal management system may vary in material and configuration provided that substantial heat is transferred to the environment from the thermal management system without excessive temperature increase at the pulse generator.

The sleeve material preferably has a bulk sound speed greater than a bulk sound speed of the core material. In a case where the sleeve is made of a material having a bulk sound speed less than a bulk sound speed of the core material, the sleeve is configured in a way that adds stiffness thereto. That is, it is known that sound speed is related to the ratio of stiffness to weight and adding stiffness to the sleeve could provide a sound speed through the sleeve greater than through the core even though the bulk sound speed through the sleeve is less than the bulk sound speed through the core. The sleeve may be stiffened by machining ridges or pockets into the interior (or the exterior) of the cladding. The voids in the cladding could be left empty or filled with a low density material.

During operation, at least a portion of the core extends into the fluid which is being measured. In a preferred implementation, the sleeve is arranged to insulate the sides of the extended core portion from heat from the fluid while leaving the tip of the core in contact with the fluid such that the insulated core portion is not cladded. This may be achieved by insulating the portion of the core sides with an air gap formed by the sleeve.

Further, in carrying out the invention, an acoustic transducer is provided in combination with an apparatus including a conduit through which fluid flows. The combination employs various features described above. The apparatus may be an exhaust gas sampling or testing apparatus.

Further, in carrying out the invention, a sampling system is provided. The system comprises a fluid inlet for receiving a fluid, a dilution inlet for receiving a dilution gas, a mixing section for mixing at least a portion of the fluid with the dilution gas, and a collection section for collecting a sample of the mixture. The system further comprises a flow meter for measuring a flow related to the sampling system. The flow meter includes an acoustic transducer for measuring the flow. The transducer employs various features described above. In one arrangement, the flow meter includes a pair of acoustic transducers arranged in an opposed fashion in a conduit through which fluid flows for measuring the flow.

Further, in carrying out the invention, a sampling system is provided. The system comprises a sample line for sampling a fluid from a main conduit, and a flow meter for measuring a flow of the fluid through the main conduit. The flow meter includes an acoustic transducer for measuring the flow. The system further comprises a dilution inlet for receiving a dilution gas, a mixing section for mixing the fluid flow from the sample line with the dilution gas at a generally fixed ratio, and a collection section for sampling the mixture. The mixture is sampled at a rate generally proportional to the flow of the fluid through the main conduit. The transducer employs various features described above. In one arrangement, the flow meter includes a pair of acoustic transducers arranged in an opposed fashion in the main conduit.

The advantages associated with embodiments of the present invention are numerous. For example, preferred embodiments of the present invention provide an acoustic transducer by shrink fitting a coaxial metal sleeve over a core of low thermal conductivity material. The cladding reduces dispersion of the acoustic pulse traveling through the core.

The above object and other objects, features, and advantages of the present invention are readily apparent from the following detailed description of the preferred embodiment when taken in connection with the accompanying drawings.

DETAILED DESCRIPTION OF THE PREFERRED EMBODIMENTS

Figure 1:
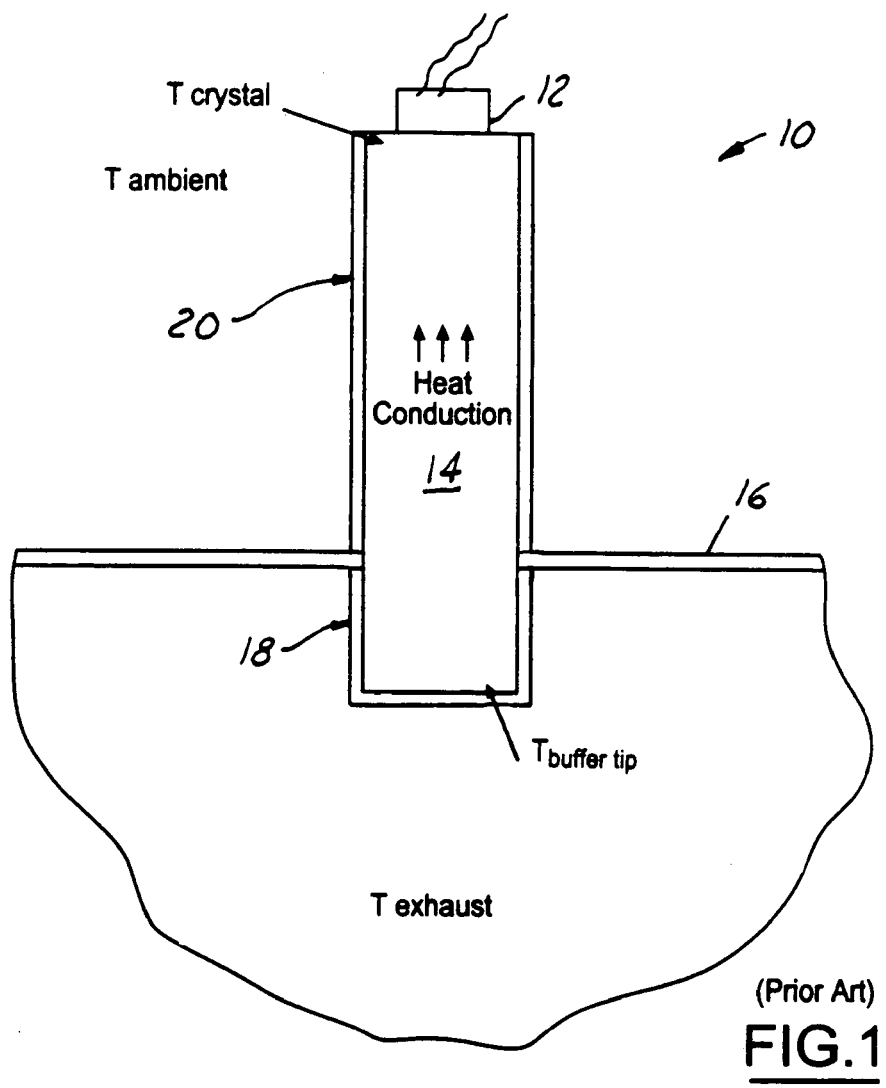
FIG. 1 illustrates a prior art use of a thermal buffer.
Figure 2:
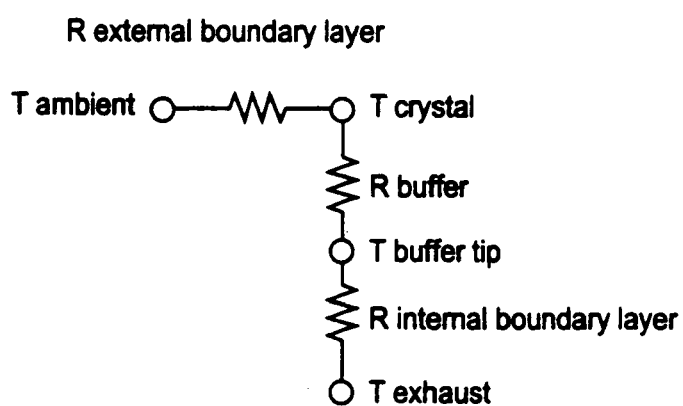
FIG. 2 illustrates an electrical equivalent circuit of the thermal buffer arrangement shown in FIG. 1.
Figure 3:
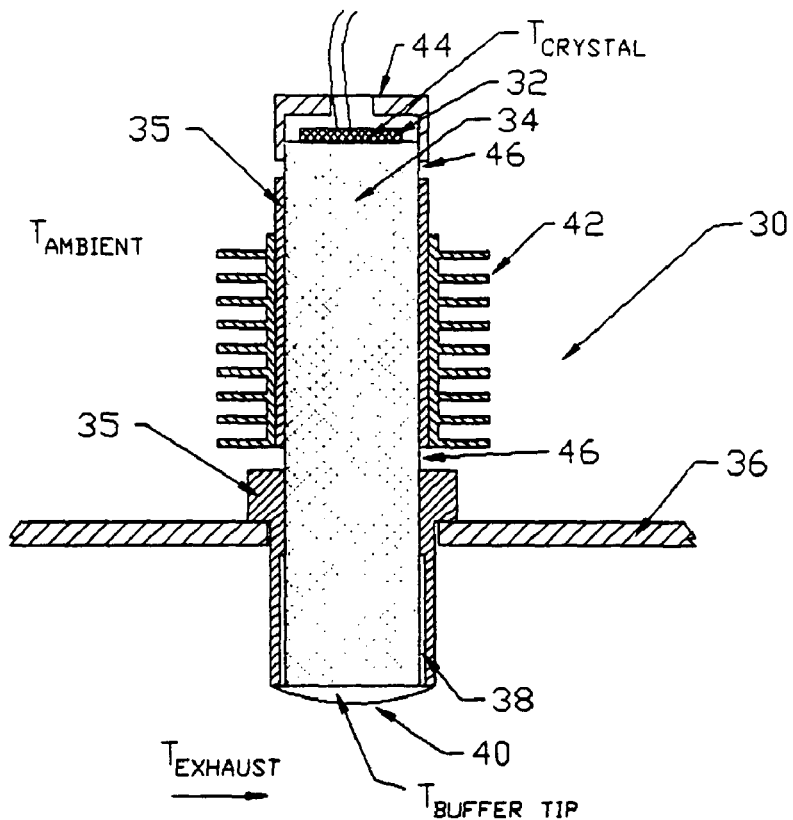
FIG. 3 illustrates an acoustic transducer in accordance with the present invention.
Figure 4:
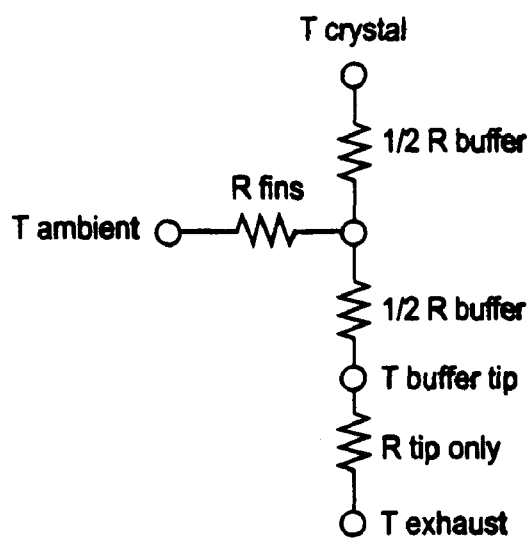
FIG. 4 illustrates an electrical equivalent circuit of the acoustic transducer arrangement shown in FIG. 3.

FIG. 3 illustrates an acoustic transducer 30 for measuring a property of a fluid. Transducer 30 includes piezoelectric element 32, and a buffer assembly composed of a core 34 and a sleeve 35. Sleeve 35 is shrink fitted over core 34 to form a cladding that reduces dispersion of the acoustic pulses traveling through core 34. The buffer assembly extends through wall 36 of a conduit through which the fluid flows. The conduit is part of an apparatus in which the acoustic transducer 30 is used. Buffer core 34 is made of a light weight, low thermal conductivity material and is preferably composed of fused silica and mica. Sleeve 35 is made of titanium and extends through wall 36 to form a metal shield 38 with a small air gap between it and the core 34 to form a high contact resistance in comparison to convective thermal boundary layer 40. The metal shield 38 also protects the buffer during installation and operation. The buffer tip is in direct contact with the fluid but could have a surface coating. Fins 42 are mounted to the sleeve 35 to dissipate heat from low on the body of core 34. A high temperature glass fusing bonds the sleeve 35 to the buffer core 34 forming a cladding and a hermitic seal with minimal contact resistance to let heat flow freely through fins 42 of the thermal management system. Housing member 44 houses piezoceramic element 32 and affixes piezoceramic element 32 against the far end of buffer core 34. Gaps 46 in the cladding layer allow heat dissipation, that is, protect the piezoceramic element or crystal from heat. FIG. 4, with an electrical equivalent circuit, illustrates the exhaust, buffer tip, crystal and ambient temperatures, and the thermal resistances of the buffer tip convective boundary layer 40, buffer assembly, and fins 42. The buffer assembly resistance is shown with part of the resistance before the fins 42 and part of the resistance after fins 42 to model the dissipation of heat from low on the body of core 34.

Figure 5:
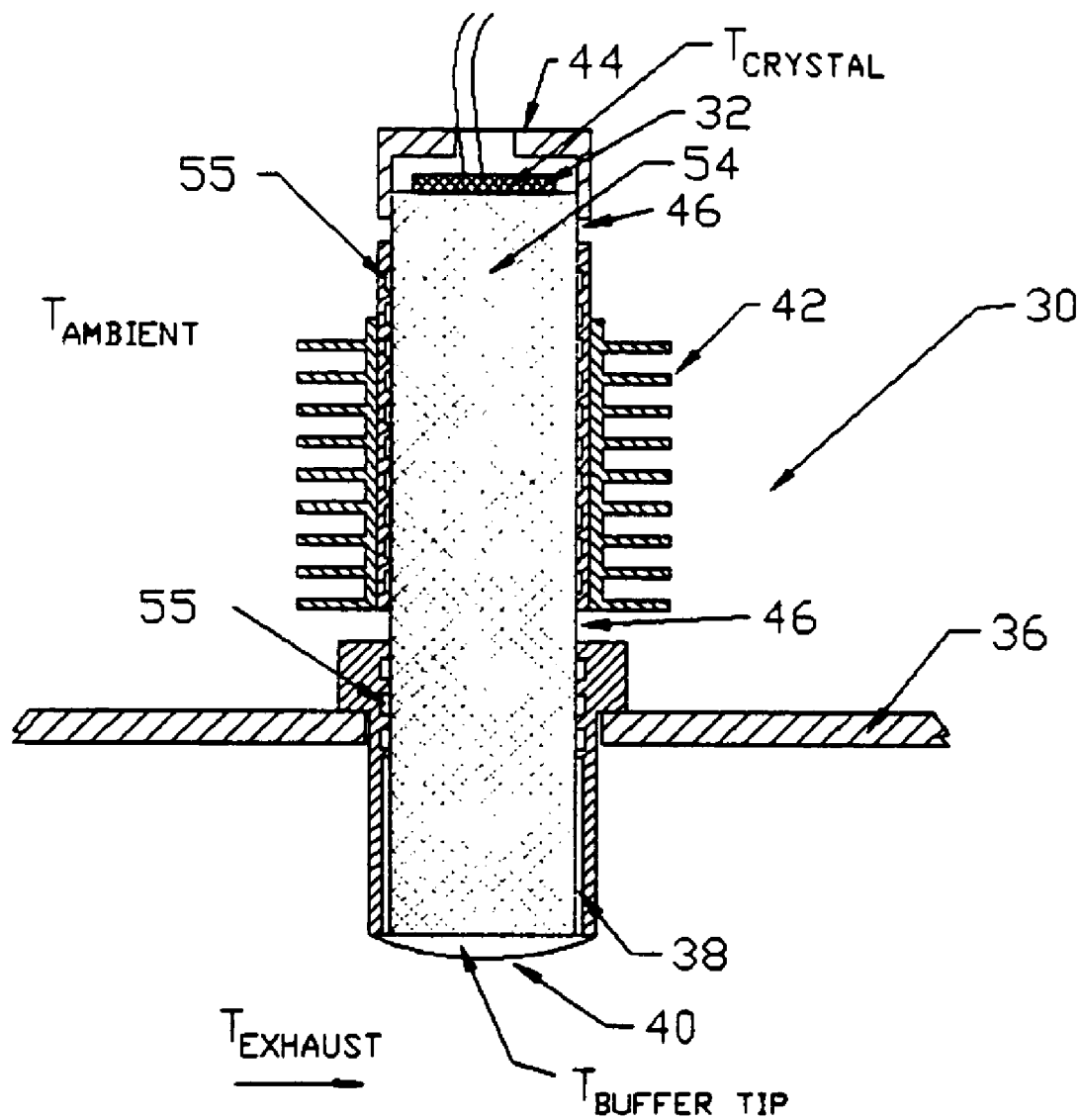
FIG. 5 illustrates an alternative acoustic transducer in accordance with the present invention.

Sleeve 35 is made of a material having a bulk sound speed greater than a bulk sound speed of core 34. FIG. 5 illustrates the case where a sleeve 55 is made of a material having a bulk sound speed less than a bulk sound speed of a core 54 with sleeve 55 configured in a way that adds stiffness thereto because sound speed through a medium corresponds to the ratio of stiffness to weight. FIG. 5 illustrates such an arrangement where sleeve 55 has pockets machined into the interior of the cladding layer. The voids in the cladding can be left empty or filled with a low density material.

Figure 6:
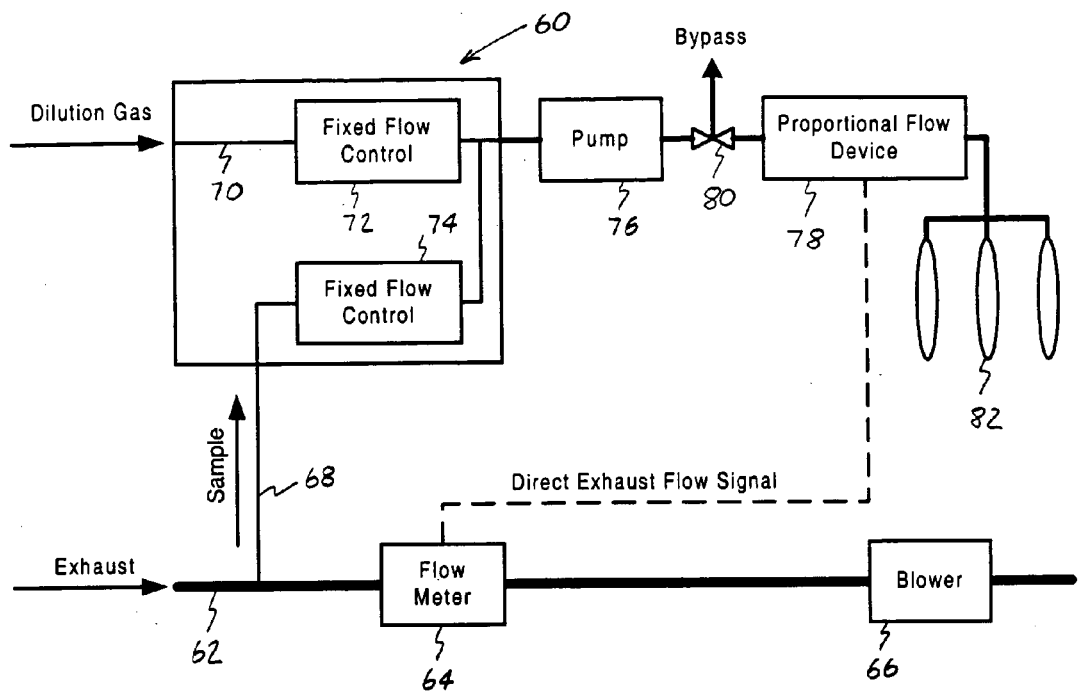
FIG. 6 illustrates a bag mini-diluter sampling system in accordance with the present invention.

FIG. 6 illustrates a bag mini-diluter sampling system at 60. Sampling system 60 includes a main conduit having an inlet 62 for receiving exhaust. Flow meter 64 measures the flow of fluid through the main conduit, and total exhaust volume is accumulated. Flow meter 64 provides a direct exhaust flow measurement signal, and includes at least one acoustic transducer of the present invention. Depending on the implementation, a blower 66 may assist fluid flow through the conduit.

A sample line 68 samples exhaust from the main conduit. A dilution inlet 70 receives a dilution gas. Fixed flow control 72 and fixed flow control 74 (mass flow controllers or critical flow venturis) control the flow of dilution gas and sampled exhaust gas, respectively, to provide a generally fixed ratio at the mixing section. Pump 76 pumps the mixture of the dilution gas and the exhaust gas sample for eventual collection in bags 82. Proportional flow device 78 provides a flow to sample collecting bags 82 that is proportional to the flow through the main conduit. Accordingly, bypass 80 is provided to allow some of the mixture to bypass the collections.

Figure 7:
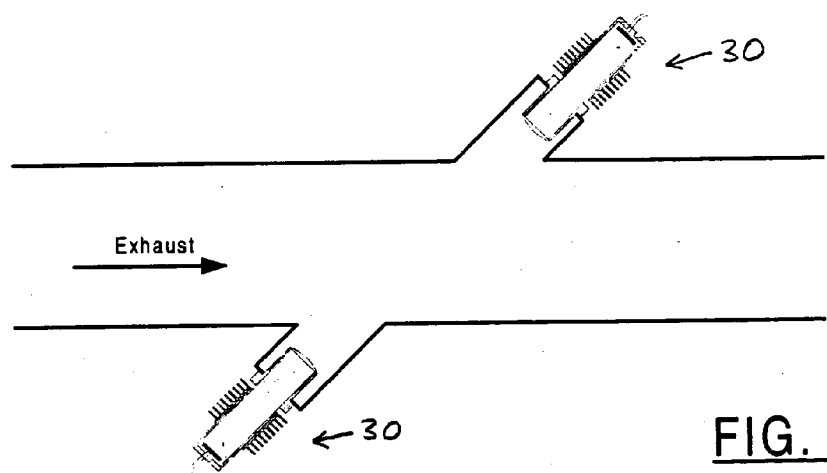
FIG. 7 illustrates the flow meter of the system of FIG. 6.

FIG. 7 illustrates flow meter 64 in greater detail showing a pair of acoustic transducers 30 arranged in an opposed fashion across the conduit.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An acoustic transducer for measuring a property of a fluid, the acoustic transducer comprising:
    an acoustic pulse generator; and
    a buffer assembly between the pulse generator and the fluid, the buffer assembly being composed of a core and a sleeve shrink fitted over the core to form a cladding that reduces dispersion of the acoustic pulses traveling through the core, the buffer assembly guiding the wave front from the pulse generator toward the fluid.

2. The acoustic transducer of claim 1 wherein the sleeve has a thermal conductivity of at least 15 W/(m·K).

3. The acoustic transducer of claim 1 wherein the sleeve is made of titanium.

4. The acoustic transducer of claim 1 wherein the core has a thermal conductivity of less than 15 W/(m·K).

5. The acoustic transducer of claim 1 wherein the core has a thermal conductivity of less than 1 W/(m·K).

6. The acoustic transducer of claim 1 wherein the core is made of fused silica.

7. The acoustic transducer of claim 6 wherein the core is made of a composite of fused silica and mica.

8. The acoustic transducer of claim 1 wherein the sleeve is secured to the core by high temperature glass fusing.

9. The acoustic transducer of claim 8 wherein the high temperature glass fusing of the sleeve and core forms a hermitic seal.

10. The acoustic transducer of claim 1 wherein the sleeve is secured to the core with a refractory cement.

11. The acoustic transducer of claim 1 wherein the sleeve is made of metal.

12. The acoustic transducer of claim 1 further comprising:
    a thermal management system mounted to the sleeve to transfer heat from the sleeve, wherein the thermal management system is formed of a high thermal conductivity material and is arranged along the sleeve such that substantial heat is transferred to the environment from the thermal management system without excessive temperature increase at the pulse generator.

13. The acoustic transducer of claim 12 wherein the thermal management system includes a plurality of fins.

14. The acoustic transducer of claim 1 wherein the sleeve is made of a material having a bulk sound speed greater than a bulk sound speed of the core material.

15. The acoustic transducer of claim 1 wherein the sleeve is made of a material having a bulk sound speed less than a bulk sound speed of the core material, and wherein the sleeve is configured in a way that adds stiffness thereto.

16. The acoustic transducer of claim 1 wherein during operation at least a portion of the core extends into the fluid which is being measured and wherein the sleeve is arranged to insulate the sides of the extended core portion from heat from the fluid while leaving the tip of the core in contact with the fluid such that the insulated core portion is not cladded.

17. The acoustic transducer of claim 1 wherein the insulated portion of the core sides is insulated by an air gap formed by the sleeve.

18. In combination with an apparatus including a conduit through which fluid flows, the improvement comprising:
    an acoustic transducer for measuring a property of a fluid, the acoustic transducer including an acoustic pulse generator and a buffer assembly between the pulse generator and the fluid, the buffer assembly being composed of a core formed of a low thermal conductivity material and a sleeve shrink fitted over the core to form a cladding that reduces dispersion of the acoustic pulses traveling through the core, the buffer assembly guiding the wave front from the pulse generator toward the fluid.

19. The combination of claim 18 wherein the sleeve is secured to the core by high temperature glass fusing.

20. The combination of claim 18 wherein the sleeve is secured to the core with a refractory cement.

21. The combination of claim 18 wherein the sleeve is made of metal.

22. The combination of claim 18 further comprising:
    a thermal management system mounted to the sleeve to transfer heat from the sleeve, wherein the thermal management system is formed of a high thermal conductivity material and is arranged along the sleeve such that substantial heat is transferred to the environment from the thermal management system without excessive temperature increase at the pulse generator.

23. The combination of claim 22 wherein the thermal management system includes a plurality of fins.

24. The combination of claim 18 wherein during operation at least a portion of the core extends into the fluid which is being measured and wherein the sleeve is arranged to insulate the sides of the extended core portion from heat from the fluid while leaving the tip of the core in contact with the fluid such that the insulated core portion is not cladded.

25. The combination of claim 18 wherein the insulated portion of the core sides is insulated by an air gap formed by the sleeve.

26. A sampling system comprising:
    a fluid inlet for receiving a fluid;
    a dilution inlet for receiving a dilution gas;
    a mixing section for mixing at least a portion of the fluid with the dilution gas;
    a collection section for collecting a sample of the mixture; and
    a flow meter for measuring a flow related to the sampling system, the flow meter including an acoustic transducer for measuring the flow, the acoustic transducer including an acoustic pulse generator and a buffer assembly between the pulse generator and the fluid, the buffer assembly being composed of a core formed of a low thermal conductivity material and a sleeve shrink fitted over the core to form a cladding that reduces dispersion of the acoustic pulses traveling through the core, the buffer assembly guiding the wave front from the pulse generator toward the fluid.

27. The sampling system of claim 26 wherein the flow meter includes a pair of acoustic transducers arranged in an opposed fashion in a conduit through which fluid flows for measuring the flow.

28. A sampling system comprising:
- a sample line for sampling a fluid from a main conduit;
- a flow meter for measuring a flow of the fluid through the main conduit, the flow meter including an acoustic transducer for measuring the flow, the acoustic transducer including an acoustic pulse generator and a buffer assembly between the pulse generator and the fluid, the buffer assembly being composed of a core formed of a low thermal conductivity material and a sleeve shrink fitted over the core to form a cladding that reduces dispersion of the acoustic pulses traveling through the core, the buffer assembly guiding the wave front from the pulse generator toward the fluid;
- a dilution inlet for receiving a dilution gas;
- a mixing section for mixing the fluid flow from the sample line with the dilution gas at a generally fixed ratio;
- a collection section for sampling the mixture, the mixture being sampled at a rate generally proportional to the flow of the fluid through the main conduit.

29. The sampling system of claim 26 wherein the flow meter includes a pair of acoustic transducers arranged in an opposed fashion in the main conduit.

* * * * *